(12) United States Patent
Hong et al.

(10) Patent No.: US 11,250,575 B2
(45) Date of Patent: Feb. 15, 2022

(54) DETERMINATION OF CONFIDENCE SCORE FOR MOTION CORRECTION

(71) Applicant: Siemens Medical Solutions USA, Inc., Malvern, PA (US)

(72) Inventors: Inki Hong, Knoxville, TN (US); Ziad Burbar, Knoxville, TN (US); Stefan B. Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 16/947,543

(22) Filed: Aug. 6, 2020

(65) Prior Publication Data

US 2021/0065380 A1 Mar. 4, 2021

Related U.S. Application Data

(60) Provisional application No. 62/891,514, filed on Aug. 26, 2019.

(51) Int. Cl.
*G06K 9/00* (2006.01)
*G06T 7/215* (2017.01)
*A61B 6/00* (2006.01)

(52) U.S. Cl.
CPC ............ *G06T 7/215* (2017.01); *A61B 6/5264* (2013.01); *G06T 2207/10081* (2013.01); *G06T 2207/10104* (2013.01)

(58) Field of Classification Search
CPC .......... G06T 7/215; G06T 2207/10081; G06T 2207/10104; G06T 2207/10108; G06T 2207/20201; G06T 5/003; G06T 7/20; A61B 6/5264
See application file for complete search history.

(56) References Cited

U.S. PATENT DOCUMENTS

| | | | |
|---|---|---|---|
| 2017/0032538 A1* | 2/2017 | Ernst | G06T 7/0012 |
| 2017/0042496 A1* | 2/2017 | Shanbhag | A61B 5/0059 |
| 2019/0261940 A1* | 8/2019 | Son | G06T 11/008 |
| 2020/0029925 A1* | 1/2020 | Saillant | G06K 9/6296 |
| 2020/0178926 A1* | 6/2020 | Kshirsagar | A61B 6/465 |

* cited by examiner

*Primary Examiner* — Atiba O Fitzpatrick

(57) ABSTRACT

A system and method include acquisition of a plurality of event data associated with an object, each of the plurality of event data associated with a position and a time, assigning of each event data to one of a plurality of time-based frames based on a time associated with the event data, each of the plurality of time-based frames associated with a respective time period, assigning of each event data to one of a plurality of motion-based frames based on a time associated with the event data, each of the plurality of motion-based frames associated with a respective time period associated with a respective motion state, determination of a confidence score based on the plurality of time-based frames of event data and on the plurality of motion-based frames of event data, and presentation of the confidence score and a control selectable to initiate motion-correction of the event data.

20 Claims, 8 Drawing Sheets

DETERMINATION OF CONFIDENCE SCORE FOR MOTION CORRECTION

CROSS-REFERENCE TO RELATED APPLICATIONS

The present application is related to and claims priority to U.S. Provisional Patent Application No. 62/891,514, filed Aug. 26, 2019, the contents of which are incorporated by reference herein for all purposes.

BACKGROUND

According to conventional nuclear imaging, a radiopharmaceutical is introduced into a patient body by injection or ingestion. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays (i.e., acquires event data) and reconstructs images based thereon.

Detection of the emitted gamma rays occurs over a period of time, during which the body may move, either inadvertently or due to natural physiological processes such as respiration and heartbeat. Such movement can lead to blurred images, particularly in the brain, abdominal, thoracic and cardiac regions. Some systems address the foregoing by systems detecting patient movement and correcting acquired event data based on the detected movement. The movement may be recorded as motion vectors occurring at particular times during the data acquisition. The motion vectors may then be used to correct the acquired data prior to image reconstruction.

Motion-correction of acquired event data can be resource- and time-intensive. Motion correction may not be needed if the body does not move significantly during imaging or if the particular application does not require high-quality reconstructed images. Accordingly, some systems might be configured to reconstruct acquired event data without first performing motion correction on the data. If the resulting reconstructed image is blurry or otherwise unsuitable, a user may instruct the system to perform motion correction on the acquired event data and to reconstruct the thusly-corrected event data. However, the resulting image may still be unsuitable, in which case the time and resources spent on the motion-correction and additional reconstruction have been wasted. Systems are desired to address the foregoing.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments estimate the effectiveness of motion correction a priori. More particularly, some embodiments estimate and provide an indication of whether application of motion-correction to event data will improve the quality of a subsequently-reconstructed image. Such an estimation and indication may advantageously allow a user to selectively initiate motion-correction in cases where motion-correction is likely to improve image quality (and where improved image quality is desired) while foregoing motion-correction in cases where motion-correction is not likely to improve image quality and/or where improved image quality is not needed, resulting in increased efficiency of resource usage.

According to some embodiments, the estimation is based on a plurality of frames of an imaging scan binned according to acquisition time (i.e., time-based frames) and on a plurality of frames of an imaging scan binned according to motion state (i.e., motion-based frames). For example, each time-based frame may include event data acquired during a unique 1 second interval, while each motion-based frame may include event data acquired during a same resting position of the imaged volume.

In a specific example, embodiments may calculate a first motion coefficient based on a plurality of time-based frames of event data and a second motion coefficient based on a plurality of motion-based frames of the event data. A confidence score is then determined based on the first motion coefficient and the second motion coefficient. The confidence score provides an indication of whether application of motion-correction to the event data will improve the quality of an image reconstructed from the event data.

Figure 1:
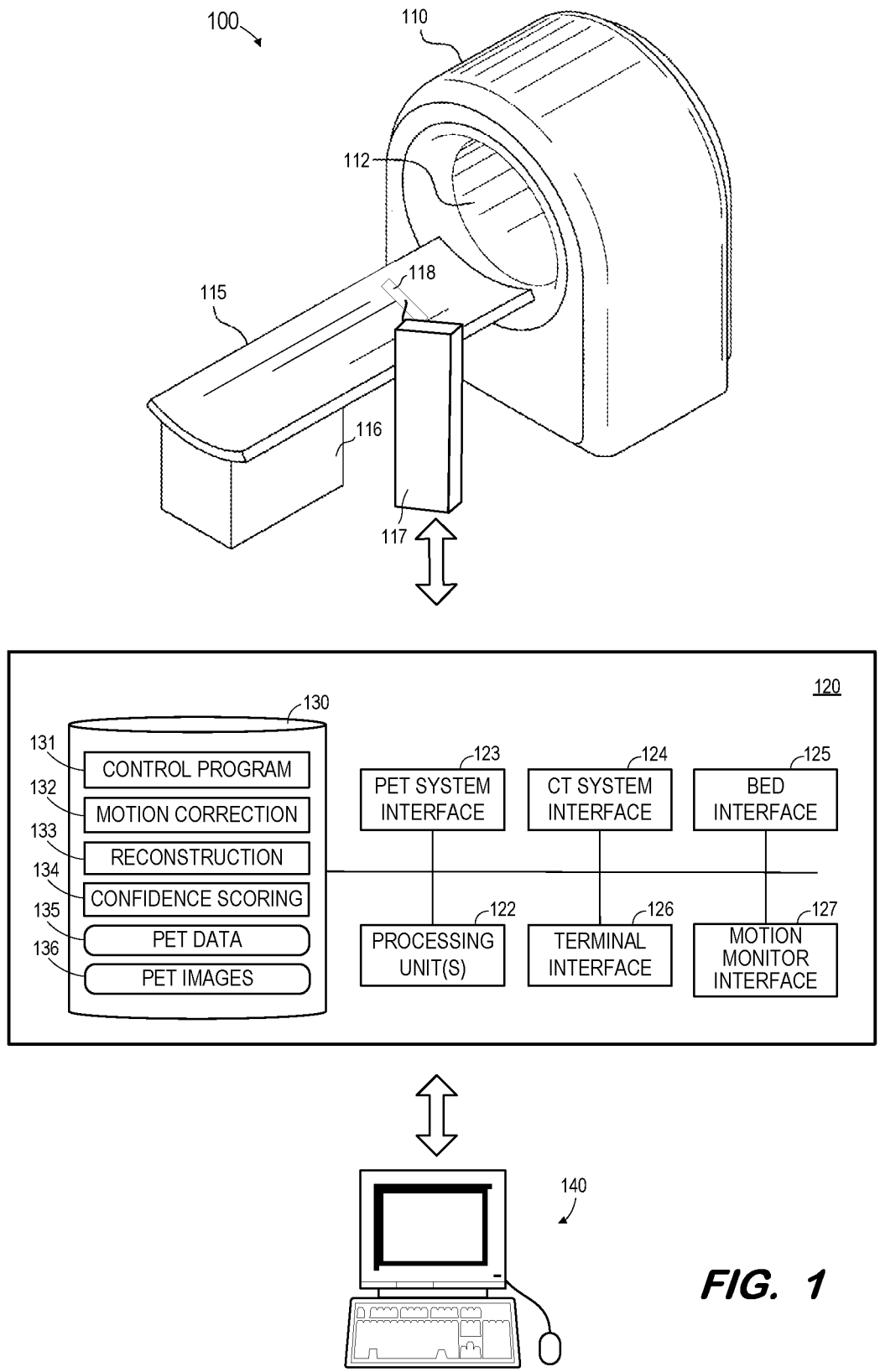
FIG. 1 is a block diagram of a PET/CT imaging system according to some embodiments.

FIG. 1 illustrates PET/CT system 100 to execute one or more of the processes described herein. Embodiments are not limited to system 100 or to a system providing two or more imaging modalities. In particular, although the acquired data described herein is referred to as event data (i.e., corresponding to gamma ray detections), embodiments are not limited to SPECT and PET imaging systems. For example, embodiments may be applied to data acquired by Computed Tomography (CT), Magnetic Resonance (MR), ultrasound or other imaging modalities, so long as the acquired image data is associated with an acquisition time and a three-dimensional position.

System 100 includes gantry 110 defining bore 112. As is known in the art, gantry 110 houses PET imaging components for acquiring PET image data and CT imaging components for acquiring CT image data. The PET imaging components may include any number of gamma cameras in any configuration as is known in the art. The CT imaging components may include one or more x-ray tubes and one or more corresponding x-ray detectors.

According to conventional PET imaging, a tracer compound including a radionuclide is introduced into a patient body by injection or ingestion. Radioactive decay of the radionuclide generates positrons, which eventually encounter electrons and are annihilated thereby. Annihilation produces two gamma photons which travel in approximately opposite directions. Accordingly, an annihilation event is identified when two detectors disposed on opposite sides of the body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Time-of-flight (TOF) PET measures the difference between the detection times of the two gamma photons arising from the annihilation event. This difference may be used to estimate a particular position along the LOR at which the annihilation event occurred. Accordingly, each annihilation event may be represented by raw (i.e., list-mode) data specifying the three-dimensional position and the time at which the event occurred.

Bed 115 and base 116 are operable to move a patient lying on bed 115 into and out of bore 112. In some embodiments, bed 115 is configured to translate over base 116 and, in other embodiments, base 116 is movable along with or alternatively from bed 115.

Movement of a patient into and out of bore 112 may allow scanning of the patient using the CT imaging elements and the PET imaging elements of gantry 110. Such scanning may proceed based on scanning parameters such as scan ranges and corresponding scanning speeds. Bed 115 and base 116 may provide continuous bed motion, as opposed to step-and-shoot motion, during such scanning according to some embodiments.

Physiological motion monitor 117 may comprise an electrocardiogram system coupled to sensor(s) 118 as is known in the art. Sensor(s) 118 may be attached to a patient as is known in the art to acquire a cardiac signal. In some embodiments, monitor 117 comprises a respiration monitor which senses a respiratory signal representing phases of breathing during image scanning. The signal(s) acquired by monitor 117 may be used to separate acquired event data into motion-based frames according to some embodiments.

Control system 120 may comprise any general-purpose or dedicated computing system. Accordingly, control system 120 includes one or more processing units 122 configured to execute processor-executable program code to cause system 120 to operate as described herein, and storage device 130 for storing the program code. Storage device 130 may comprise one or more fixed disks, solid-state random-access memory, and/or removable media (e.g., a thumb drive) mounted in a corresponding interface (e.g., a USB port).

Storage device 130 stores program code of control program 131. One or more processing units 122 may execute control program 131 to, in conjunction with PET system interface 123, bed interface 125, and monitor interface 127, control hardware elements to move a patient into bore 112 and, during the movement, control gamma cameras to rotate around bore 112 and to detect coincidence events occurring within a body located in bore 112. The detected events may be stored in memory 130 as PET data 135, which may comprise list-mode data and/or sinograms.

One or more processing units 122 may also execute control program 131 to, in conjunction with CT system interface 124, cause a radiation source within gantry 110 to emit radiation toward a body within bore 112 from different projection angles, and to control a corresponding detector to acquire two-dimensional CT data. The CT data may be acquired substantially contemporaneously with the PET data as described above.

Storage device 130 also includes motion correction program 132 for correcting acquired PET data based on motion information. For example, embodiments may determine a motion vector representing patient motion between a first time period and a second time period. Motion correction program 132 may be executed to correct PET data acquired during the second time period based on the motion vector, such that the corrected data is registered with PET data acquired during the first time period.

Reconstruction program 133 may be executed to reconstruct PET images 136 from PET data 135 using any reconstruction algorithm that is or becomes known. Confidence scoring program 134 determines a confidence score based on PET data 135 as described herein. The confidence score may provide an indication of a likelihood that application of motion correction to PET data will result in a more desirable PET image than if motion-correction were not applied.

PET images, confidence scores and CT images may be transmitted to terminal 140 via terminal interface 126. Terminal 140 may comprise a display device and an input device coupled to system 120. Terminal 140 may display PET images, CT images, confidence scores, and/or any other suitable images or data. Terminal 140 may receive user input for controlling display of the data, operation of system 100, and/or execution of motion-correction in response to a determined confidence score. In some embodiments, terminal 140 is a separate computing device such as, but not limited to, a desktop computer, a laptop computer, a tablet computer, and a smartphone.

Each component of system 100 and of each other system described herein may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Figure 2:
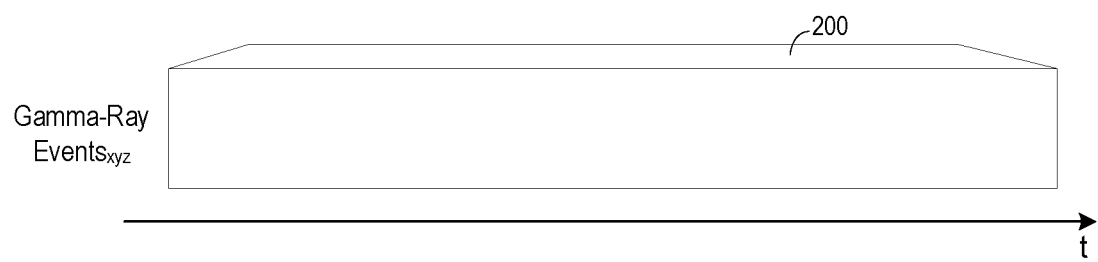
FIG. 2 illustrates event data acquired over time according to some embodiments.

FIG. 2 is a representation of acquired event data 200 for purposes of describing some embodiments. Event data 200 describes events detected by a PET or SPECT scanner. Each event is described by an event time (i.e., the time at which the event occurred) denoted by its position along axis t, and a three-dimensional event position represented by the three-dimensional graphic of FIG. 2. The event position may be represented using any suitable coordinate system such as but not limited to a coordinate system of imaging system 100. Event data 200 may be acquired in list-mode as is known in the art.

Figure 3:
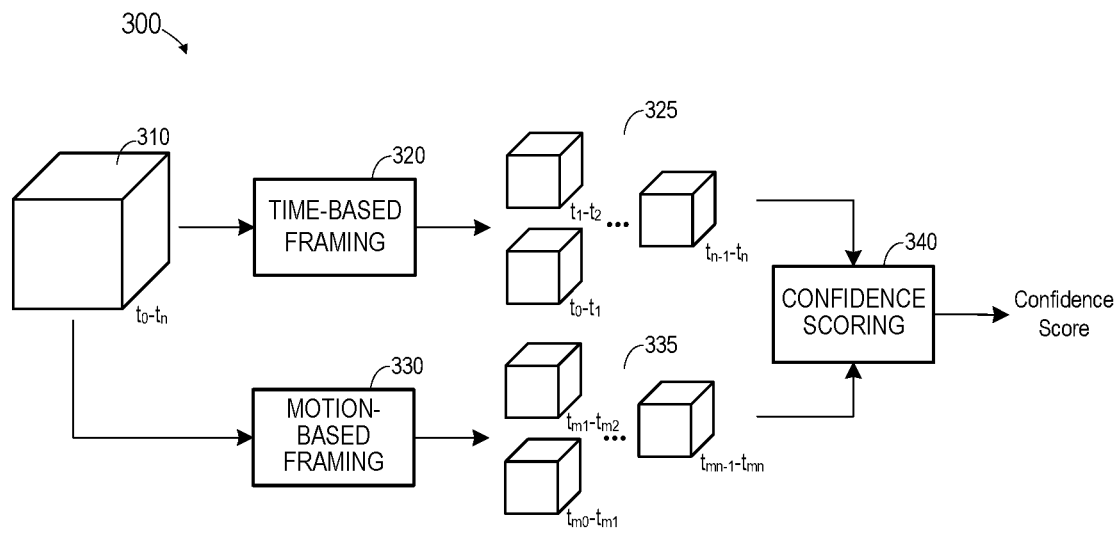
FIG. 3 illustrates a system to determine a motion correction confidence score based on event data according to some embodiments.

FIG. 3 is a block diagram of system 300 according to some embodiments. Event data 310 represents a set of image data in which each event is associated with a position and an acquisition time (i.e., between time to and time $t_n$). Event data 310 may be formatted in list-mode or as a sinogram. That is, although represented as a three-dimensional volume, event data 310 merely consists of data from which a three-dimensional volume may be reconstructed.

Event data 310 is independently subjected to time-based framing 320 and to motion-based framing 330. As shown, time-based framing 320 results in a plurality of individual time-based frames 325. Each of time-based frames 325 is associated with a unique time period (e.g., $t_0$-$t_1$, $t_1$-$t_2$) between time $t_0$ and time $t_n$ and consists of event data of event data 310 which is associated with the unique time period.

Motion-based framing 330 results in a plurality of individual motion-based frames 335. Each of motion-based frames 335 is associated with a unique motion state and a time period during which the imaged object was disposed in the motion state (e.g., $t_{m0}$-$t_{m1}$, $t_{m1}$-$t_{m2}$). A motion state may consist of a position of the object in between periods of motion, and the associated time periods may differ among different motion states. For example, an object may reside in a first position for 3 seconds, move for 1 second, and reside in a second motion state for 5 seconds before moving again. In this example, the time period of the first motion state is 3 seconds and the time period of the second motion state is 5 seconds. Each of motion-based frames 335 consists of event data of event data 310 which is associated with the unique time period during which the object was disposed in the associated motion state.

Confidence scoring 340 determines a confidence score based on the plurality of individual time-based frames 325 and the plurality of individual motion-based frames 335. Various techniques for determining the confidence score will be described below.

Figure 4:
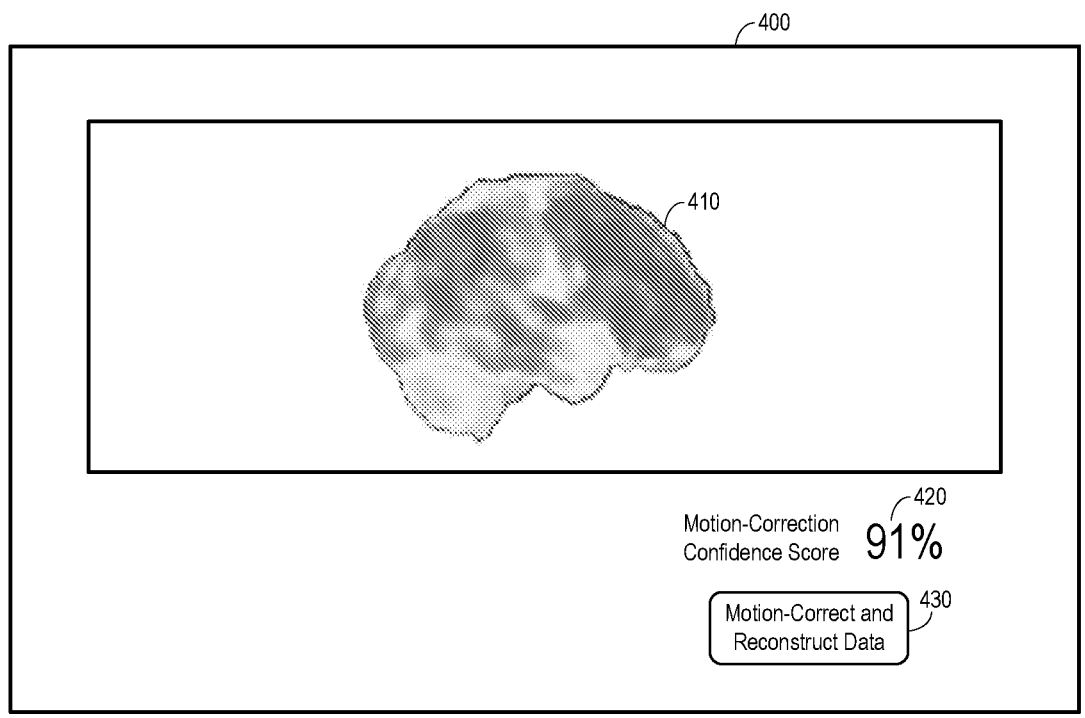
FIG. 4 is a view of a user interface presenting a two-dimensional representation of a three-dimensional volume and a motion correction confidence score according to some embodiments.

FIG. 4 is an example of user interface 400 according to some embodiments. Terminal 140 may display user interface 400 to a user. User interface 400 shows representation 410 of a three-dimensional volume reconstructed based on acquired event data. It will be assumed that motion-correction was not applied to the event data prior to reconstruction.

It will also be assumed that confidence score 420 was determined based on the acquired event data as described herein. Confidence score 420 provides an indication of the likelihood of improving image 410 by performing motion-correction on the event data and re-performing reconstruction on the motion-corrected event data. User interface 400 also provides control 430. According to some embodiments, a user may select control 430 to initiate motion-correction on the event data and re-perform the reconstruction on the motion-corrected event data. The initiated motion correction may comprise any motion correction that is or becomes known, including but not limited to inelastic motion correction and elastic motion correction. In some embodiments, a high confidence score may indicate that the data represents such a high degree of motion that the data should be discarded.

Figure 5:
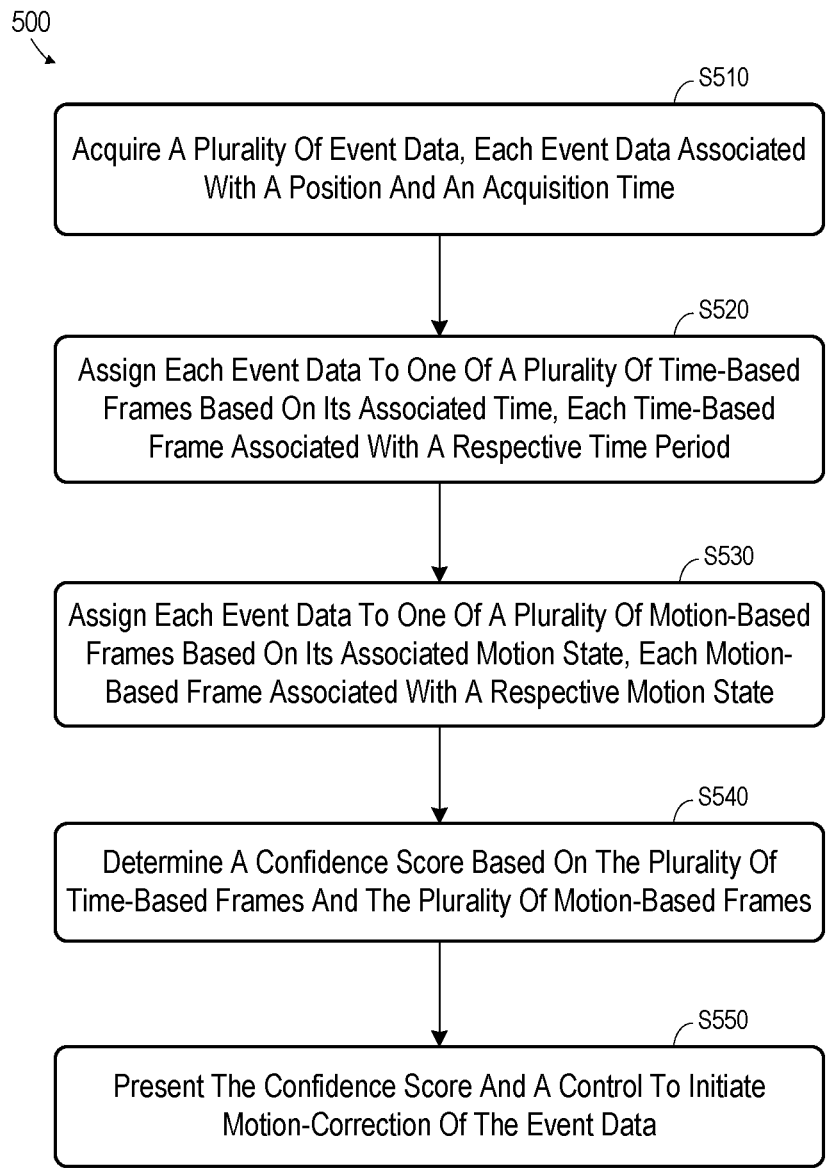
FIG. 5 comprises a flow diagram of a process to determine a motion correction confidence score based on time-based frames and motion-based frames of event data according to some embodiments.

FIG. 5 comprises a flow diagram of process 500 to determine a motion correction confidence score based on time-based frames and motion-based frames of event data according to some embodiments. Flow diagram 500 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape. Embodiments are not limited to the examples described below.

Initially, a plurality of event data is acquired at S510. The acquired event data may comprise, in some embodiments, list-mode PET data as described above. The event data may be acquired by an imaging system separate from a system used to perform the remainder of process 500. For example, the event data may be originally acquired in an imaging theatre, with process 500 being executed hours, days, months, etc. after the acquisition. Moreover, although the acquired data is described as event data, any data associated with an acquisition time and position may be acquired at S510.

Figure 6:
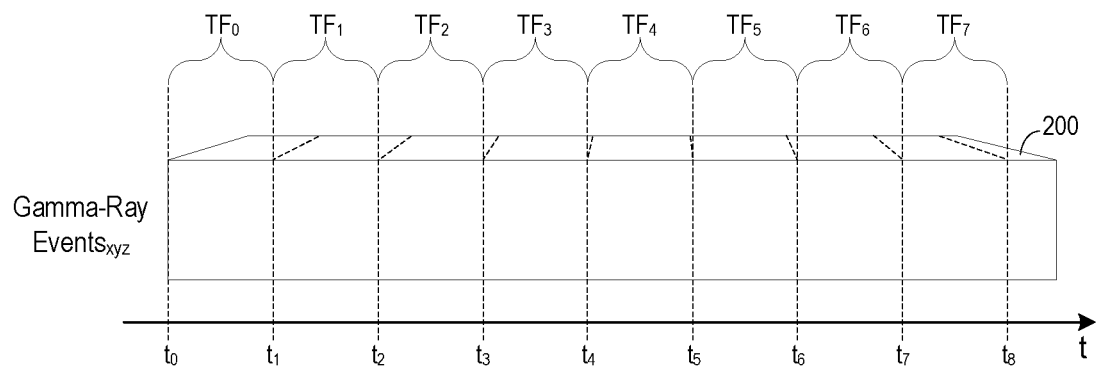
FIG. 6 illustrates time-based framing of event data according to some embodiments.

Next, at S520, each event data is assigned to (i.e., associated with) one of a plurality of time-based frames. Each of the plurality of frames is associated with a time period, and the data of one event is assigned to a particular frame that is associated with a time period including the time of the one event. FIG. 6 illustrates assignment of event data 200 of FIG. 2 to time-based frames $TF_0$ through $TF_7$ at S520 according to some embodiments.

Each of time-based frames $TF_0$ through $TF_7$ includes respective portions of data 200. Frame $TF_0$ includes all event data acquired between time $t_0$ and $t_1$, frame $TF_1$ includes all event data acquired between time $t_1$ and $t_2$, etc. In some embodiments, each frame represents a 1s time period, and dozens of frame may be used. Embodiments are not limited to a fixed frame duration, to any particular duration, or to any particular number of time-based frames.

Each of the acquired event data is assigned to one of a plurality of motion-based frames at S530 based on its associated motion state. S530 may therefore include determination of a motion state associated with each event data. In some embodiments, the acquired event data is analyzed using known techniques to identify periods of motion and periods of relative stasis. Each period of relative stasis is identified as a unique motion state and the event data acquired during that period is considered as associated with the motion state. According to some embodiments, an external monitoring system such as a respiration belt, a camera system or a cardiac monitor identifies time periods of patient movement and relative stasis, and those time periods are used to determine the event data associated with each motion state.

Figure 7:
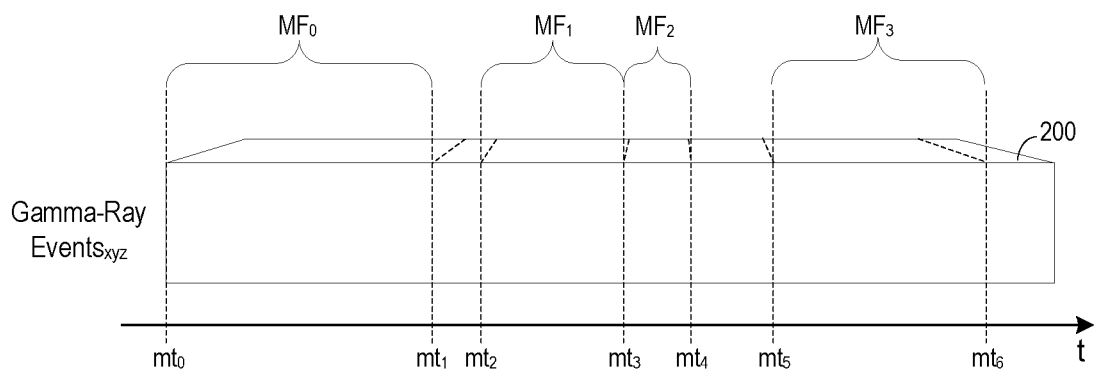
FIG. 7 illustrates motion-based framing of event data according to some embodiments.

FIG. 7 illustrates assignment of event data 200 of FIG. 2 to motion-based frames $MF_0$ through $MF_3$ at S530 according to some embodiments. Frame $MF_0$ includes all event data acquired between time $mt_0$ and $mt_1$, which is a time period associated with a first motion state. It will be assumed that the imaged object moved to an unsuitable degree between time $mt_1$ and $mt_2$ and therefore no motion state is associated with that time period or with the event data acquired during that time period. Frame $MF_1$ includes all event data acquired between time $mt_2$ and $mt_3$, which is a time period associated with a second motion state.

Figure 8:
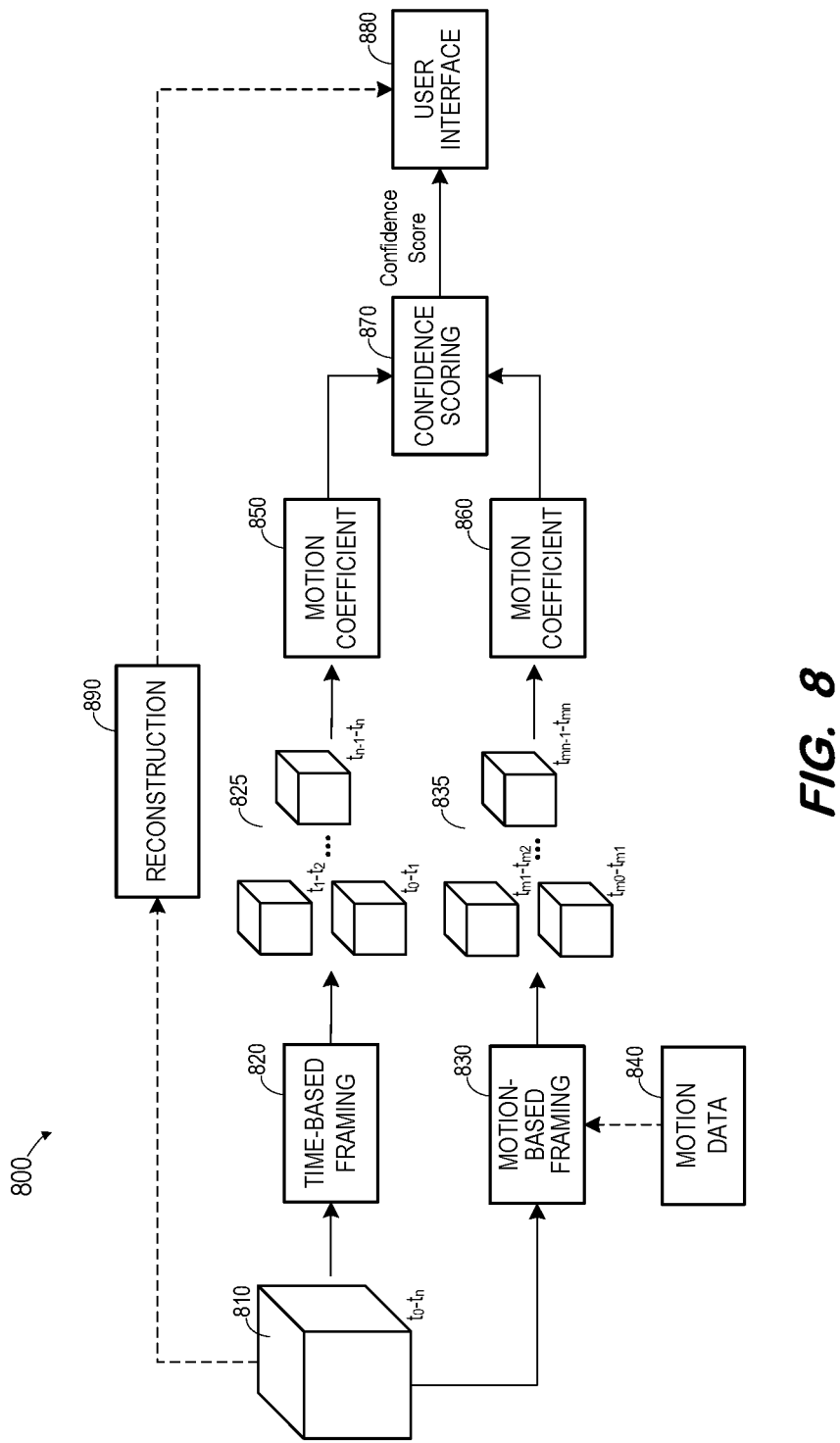
FIG. 8 illustrates a system to determine a motion correction confidence score based on time-based frames and motion-based frames of event data according to some embodiments.

A confidence score is determined at S540 based on the plurality of time-based frames and the plurality of motion-based frames. Any suitable algorithm that is or becomes known may be used at S540 to determine a confidence score. FIG. 8 illustrates system 800 according to some embodiments. System 800 may comprise an implementation of system 300 but embodiments are not limited thereto.

As shown in FIG. 8, event data 810 is framed into time-based frames 825 and motion-based frames 835 at S520 and S530. Motion-based framing 830 may optionally utilize externally-acquired motion data 840 to determine the time periods associated with each motion-based frame 835 as described above.

Next, at S540, motion coefficient component 850 determines a motion coefficient based on time-based frames 825. The motion coefficient may relate to an amount of motion represented within time-based frames 825. Also at S540, motion coefficient component 860 determines a motion coefficient based on motion-based frames 835. The motion coefficient determined by component 860 may relate to an amount of motion represented within motion-based frames 825. Confidence scoring 870 then determines the confidence score at S540 based on the two motion coefficients and using any suitable algorithm.

The confidence score is presented at S550, along with a control to initiate motion-correction of the event data. As described above, if the confidence score indicates that notion-correction would provide a better reconstructed image and such an image is desired, a user may select the control to initiate motion-correction and reconstruction of the motion-corrected event data. As mentioned above, the confidence score may indicate that the data should be discarded. A non-motion-corrected reconstructed image may also be presented at S550 according to some embodiments and as shown in FIG. 4. In this regard, of FIG. 8 indicates optional reconstruction of event data 810 by reconstruction component 890 for presentation along with the confidence score and control on user interface 860.

Figure 9A:
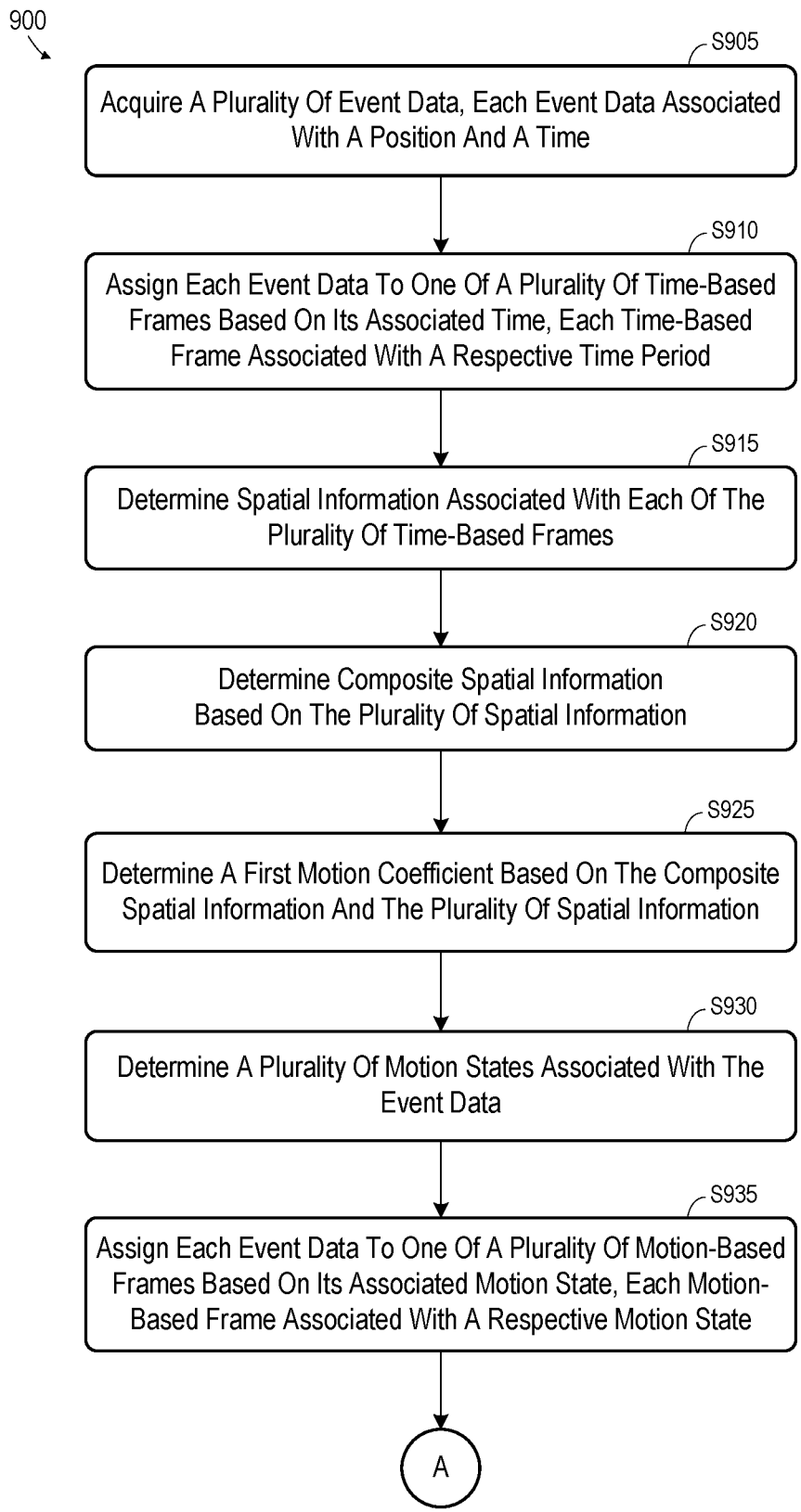
FIGS. 9A and 9B comprise a flow diagram of a process to determine a motion correction confidence score based on time-based frames and motion-based frames of event data according to some embodiments.
Figure 9B:
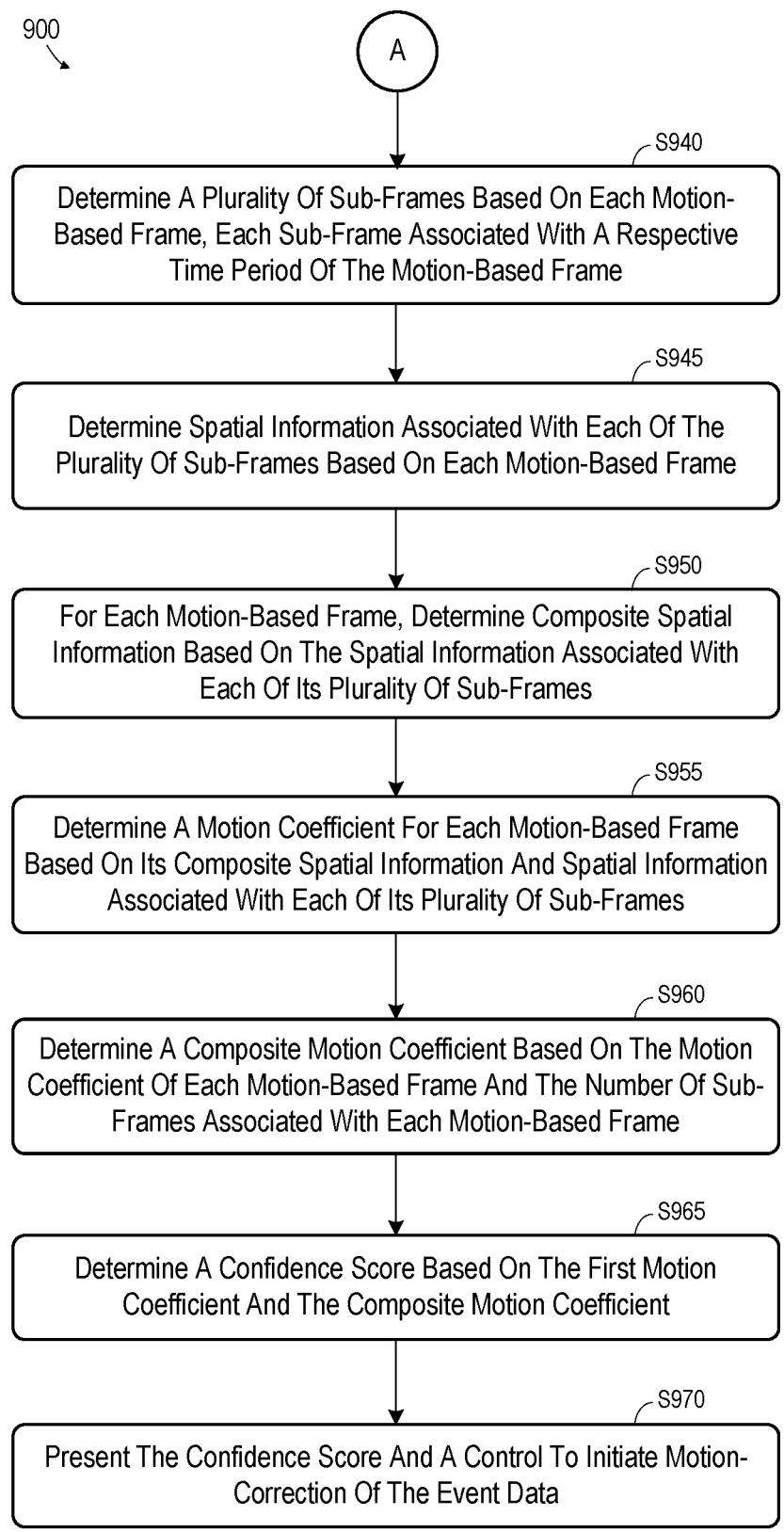

FIGS. 9A and 9B comprise a flow diagram of process 900 to determine a motion correction confidence score based on time-based frames and motion-based frames of event data according to some embodiments. Process 900 may comprise an implementation of process 500, but embodiments are not limited thereto.

Initially, a plurality of event data is acquired at S905 as described with respect to S510. Each event data is assigned to one of a plurality of time-based frames at S910 based on its acquisition time, as described with respect to S520.

Spatial information associated with each of the plurality of time-based frames is determined at S915. The determination may be based on positions associated with the event data assigned to each frame. In one non-exhaustive example, S915 comprises determination of a spatial position associated with frame $TF_0$ based on the positions associated with each event data assigned to frame $TF_0$. In this regard, each event data of frame $TF_0$ is associated with a three-dimensional position. Accordingly, the spatial position determined at S915 is a three-dimensional position around which the positions of each event data of frame $TF_0$ are equally distributed (i.e., a centroid of distribution). The determination at S915 may employ any suitable algorithm that is or becomes known.

S915 may comprise the determination of any spatial characteristic or characteristics associated with each time-based frame. The characteristic may be a representative position other than a geometric center of distribution. The spatial information determined for each frame at S915 may comprise a value/vector/equation representing a spatial entity that allows identification and quantification of motion between frames of event data.

Composite spatial information is determined at S920 based on the spatial information determined for each of the plurality of time-based frames at S915. Determination of the composite spatial information at S915 depends on the nature of the spatial information determined at S915. In one example, the composite spatial information is determined as the average of the spatial information determined at S915 (e.g., the centroid of centroids).

A first motion coefficient is determined at S925 based on the composite spatial information and the plurality of spatial information determined at S915. According to some embodiments, the first motion coefficient is a measure of the overall deviance of the plurality of spatial information determined at S915 from the composite spatial information. For example, the first motion coefficient may be determined at S925 as the root-mean-square error between the plurality of spatial information and the composite spatial information. Embodiments are not limited to any particular algorithm for determining the first motion coefficient at S925.

Each of the acquired event data is assigned to one of a plurality of motion-based frames at S935. The assignment at S935 may proceed as described with respect to S530, with the time periods associated with each motion state determined based on the event data itself and/or on externally-acquired motion information.

At S940, a plurality of sub-frames are determined based on each motion-based frame. A sub-frame of a motion-based frame includes the event data for a particular time period of the motion-based frame. For example, in the case of a motion-based frame including event data acquired over a 10 second period, S940 may comprise determination of 10 sub-time frames, with each sub-frame comprising event data of one second of the 10 seconds. The number of sub-frames and the time period associated with each sub-frame may differ across each motion-based frame, and the time periods associated with each sub-frame of a single motion-based frame may also differ from one another.

Next, at S945, spatial information associated with each sub-frame of each motion-based frame is determined. The spatial information may be determined as described above with respect to S915. In some embodiments, both S915 and S945 comprise determining the centroid of each subject frame.

Composite spatial information is determined at S950 for each of the motion-based frames. The composite spatial information for a given motion-based frame is determined based on the spatial information determined for each of the sub-frames of the motion-based frame. The composite spatial information may be determined at S950 as described above with respect to S920. For example, both S920 and S950 may comprise determination of a centroid of centroids.

At S955, a motion coefficient is determined for each motion-based frame based on its determined composite spatial information and on the spatial information determined for each of its sub-frames. As described with respect to S925, the motion coefficient for a motion-based frame may be determined based on a root-mean-square error between the composite spatial information of the motion-based frame and the spatial information determined for each of its sub-frames.

A composite motion coefficient is determined at S960 based on the motion coefficient determined for each motion-based frame and the number of sub-frames associated with each motion-based frame. In one example of S960, the motion coefficient determined for each motion-based frame is multiplied by the number of sub-frames associated with the motion-based frame. These products are summed and then divided by the total number of sub-frames associated with all motion-based frames to generate the composite motion coefficient.

A confidence score is determined at S965 based on the first motion coefficient determined at S925 and the composite motion coefficient determined at S960. Any suitable algorithm may be employed at S965 to determine the confidence score. In one example, the confidence score is determined as (first motion coefficient−composite motion coefficient)/(first motion coefficient). This calculation provides a confidence score in which the proximity to a value of 1 is directly related to a degree of improvement in the reconstructed image which is expected to result from motion-correction.

As described with respect to S550, the confidence score is presented at S970 along with a control to initiate motion correction of the event data (and subsequent image reconstruction).

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   an imaging device to:
   acquire a plurality of event data associated with an object, each of the plurality of event data associated with a position and a time; and
   a processing system to:
   assign each event data to one of a plurality of time-based frames based on a time associated with the event data, each of the plurality of time-based frames associated with a respective time period;
   assign each event data to one of a plurality of motion-based frames based on a time associated with the event data, each of the plurality of motion-based frames associated with a respective time period associated with a respective motion state; and
   determine a confidence score based on the plurality of time-based frames of event data and on the plurality of motion-based frames of event data; and
   a display to:
   present the confidence score and a control selectable to initiate motion-correction of the event data.

2. A system according to claim 1, further comprising:
   a motion monitor to output motion data based on motion of the object,
   wherein the processing system is further to determine the respective time periods associated with respective motion states based on the motion data.

3. A system according to claim 1, the processing system to:
   determine a first motion coefficient based on the plurality of time-based frames; and
   determine a second motion coefficient based on the plurality of motion-based frames,
   wherein the confidence score is determined based on first motion coefficient and the second motion coefficient.

4. A system according to claim 3, wherein determination of the first motion coefficient comprises:
   determination of spatial information associated with each of the plurality of time-based frames;
   determination of composite spatial information based on the determined spatial information; and
   determination of the first motion coefficient based on a difference between the spatial information associated with each of the plurality of time-based frames and the composite spatial information.

5. A system according to claim 4, wherein determination of the second motion coefficient comprises:
   determination of a plurality of sub-frames from each of the motion-based frames;
   determination of spatial information associated with each of the plurality of sub-frames;
   determination of composite spatial information for each of the motion-based frames based on the spatial information determined for respective sub-frames;
   determine a motion coefficient for each of the motion-based frames based on a difference between the spatial information associated with each of a respective plurality of sub-frames and the composite spatial information determined for the motion-based frame; and
   determination of the second motion coefficient based on the motion coefficient determined for each of the motion-based frames and on a number of sub-frames associated with each of the motion-based frames.

6. A system according to claim 3, wherein determination of the second motion coefficient comprises:
   determination of a plurality of sub-frames from each of the motion-based frames;
   determination of spatial information associated with each of the plurality of sub-frames;
   determination of composite spatial information for each of the motion-based frames based on the spatial information determined for respective sub-frames;
   determination of a motion coefficient for each of the motion-based frames based on a difference between the spatial information associated with each of a respective plurality of sub-frames and the composite spatial information determined for the motion-based frame; and
   determination of the second motion coefficient based on the motion coefficient determined for each of the motion-based frames and on a number of sub-frames associated with each of the motion-based frames.

7. A system according to claim 1, the processing system further to reconstruct an image based on the event data; and
   the display further to present the image simultaneously with the confidence score and the control.

8. A method comprising:
   acquiring a plurality of event data associated with an object, each of the plurality of event data associated with a position and a time;
   assigning each event data to one of a plurality of time-based frames based on a time associated with the event data, each of the plurality of time-based frames associated with a respective time period;
   assigning each event data to one of a plurality of motion-based frames based on a time associated with the event data, each of the plurality of motion-based frames associated with a respective time period associated with a respective motion state;
   determining a confidence score based on the plurality of time-based frames of event data and on the plurality of motion-based frames of event data; and
   presenting, to a user, the confidence score and a control selectable to initiate motion-correction of the event data.

9. A method according to claim 8, further comprising:
   monitoring motion of the object; and
   determining he respective time periods associated with respective motion states based on the monitored motion.

10. A method according to claim 8, further comprising:
    determining a first motion coefficient based on the plurality of time-based frames; and
    determining a second motion coefficient based on the plurality of motion-based frames,
    wherein the confidence score is determined based on first motion coefficient and the second motion coefficient.

11. A method according to claim 10, wherein determining the first motion coefficient comprises:
    determining spatial information associated with each of the plurality of time-based frames;
    determining composite spatial information based on the determined spatial information; and
    determining the first motion coefficient based on a difference between the spatial information associated with each of the plurality of time-based frames and the composite spatial information.

12. A method according to claim 11, wherein determining the second motion coefficient comprises:
  determining a plurality of sub-frames from each of the motion-based frames;
  determining spatial information associated with each of the plurality of sub-frames;
  determining composite spatial information for each of the motion-based frames based on the spatial information determined for respective sub-frames;
  determining a motion coefficient for each of the motion-based frames based on a difference between the spatial information associated with each of a respective plurality of sub-frames and the composite spatial information determined for the motion-based frame; and
  determining the second motion coefficient based on the motion coefficient determined for each of the motion-based frames and on a number of sub-frames associated with each of the motion-based frames.

13. A method according to claim 10, wherein determining the second motion coefficient comprises:
  determining a plurality of sub-frames from each of the motion-based frames;
  determining spatial information associated with each of the plurality of sub-frames;
  determining composite spatial information for each of the motion-based frames based on the spatial information determined for respective sub-frames;
  determining a motion coefficient for each of the motion-based frames based on a difference between the spatial information associated with each of a respective plurality of sub-frames and the composite spatial information determined for the motion-based frame; and
  determining the second motion coefficient based on the motion coefficient determined for each of the motion-based frames and on a number of sub-frames associated with each of the motion-based frames.

14. A method according to claim 8, further comprising:
  reconstructing an image based on the event data; and
  presenting the image simultaneously with the confidence score and the control.

15. A non-transitory computer-readable medium storing processor-executable process steps executable to cause a computing system to:
  acquire a plurality of event data associated with an object, each of the plurality of event data associated with a position and a time;
  assign each event data to one of a plurality of time-based frames based on a time associated with the event data, each of the plurality of time-based frames associated with a respective time period;
  assign each event data to one of a plurality of motion-based frames based on a time associated with the event data, each of the plurality of motion-based frames associated with a respective time period associated with a respective motion state;
  determine a confidence score based on the plurality of time-based frames of event data and on the plurality of motion-based frames of event data; and
  present the confidence score and a control selectable to initiate motion-correction of the event data.

16. A non-transitory computer-readable medium according to claim 15, the processor-executable process steps further executable to cause a computing system to:
  monitor motion of the object; and
  determine the respective time periods associated with respective motion states based on the monitored motion.

17. A non-transitory computer-readable medium according to claim 15, the processor-executable process steps further executable to cause a computing system to:
  determine a first motion coefficient based on the plurality of time-based frames; and
  determine a second motion coefficient based on the plurality of motion-based frames, wherein the confidence score is determined based on first motion coefficient and the second motion coefficient.

18. A non-transitory computer-readable medium according to claim 17, wherein determination of the first motion coefficient comprises:
  determination of spatial information associated with each of the plurality of time-based frames;
  determination of composite spatial information based on the determined spatial information; and
  determination of the first motion coefficient based on a difference between the spatial information associated with each of the plurality of time-based frames and the composite spatial information.

19. A non-transitory computer-readable medium according to claim 18, wherein determination of the second motion coefficient comprises:
  determination of a plurality of sub-frames from each of the motion-based frames;
  determination of spatial information associated with each of the plurality of sub-frames;
  determination of composite spatial information for each of the motion-based frames based on the spatial information determined for respective sub-frames;
  determine a motion coefficient for each of the motion-based frames based on a difference between the spatial information associated with each of a respective plurality of sub-frames and the composite spatial information determined for the motion-based frame; and
  determination of the second motion coefficient based on the motion coefficient determined for each of the motion-based frames and on a number of sub-frames associated with each of the motion-based frames.

20. A non-transitory computer-readable medium according to claim 17, wherein determination of the second motion coefficient comprises:
  determination of a plurality of sub-frames from each of the motion-based frames;
  determination of spatial information associated with each of the plurality of sub-frames;
  determination of composite spatial information for each of the motion-based frames based on the spatial information determined for respective sub-frames;
  determination of a motion coefficient for each of the motion-based frames based on a difference between the spatial information associated with each of a respective plurality of sub-frames and the composite spatial information determined for the motion-based frame; and
  determination of the second motion coefficient based on the motion coefficient determined for each of the motion-based frames and on a number of sub-frames associated with each of the motion-based frames.

* * * * *